United States Patent [19]

Di Mino et al.

[11] Patent Number: 5,249,575

[45] Date of Patent: Oct. 5, 1993

[54] CORONA DISCHARGE BEAM THERMOTHERAPY SYSTEM

[75] Inventors: Alfonso Di Mino; Andre Di Mino, both of Woodcliff Lake, N.J.

[73] Assignee: ADM Tronics Unlimited, Inc., Northvale, N.J.

[21] Appl. No.: 779,841

[22] Filed: Oct. 21, 1991

[51] Int. Cl.$^5$ .............................................. A61N 1/02
[52] U.S. Cl. ................................................ 607/150
[58] Field of Search ............... 128/422, 800, 804, 399, 128/783, 419 R, 423 R

[56] References Cited

U.S. PATENT DOCUMENTS

| | | | |
|---|---|---|---|
| 3,563,246 | 2/1971 | Puharich | 128/422 |
| 3,617,684 | 11/1971 | Di Mino | 219/121.11 |
| 3,676,633 | 7/1972 | Di Mino | 219/121.36 X |
| 3,991,770 | 11/1976 | LeVeen | 128/422 X |
| 4,249,537 | 2/1981 | Lee et al. | 128/422 |
| 4,531,524 | 7/1985 | Mioduski | 128/422 |
| 4,667,677 | 5/1987 | Di Mino | 128/419 R |
| 4,887,603 | 12/1989 | Morawetz et al. | 128/422 |

Primary Examiner—Lee S. Cohen
Assistant Examiner—Jeffrey R. Jastrzab
Attorney, Agent, or Firm—Michael Ebert

[57] ABSTRACT

A corona discharge beam thermotherapy system adapted to project the beam onto the skin surface of a living body overlying a problem region, the beam serving to relieve pain and to obtain other beneficial effects. The system includes an energy-generating unit in which a radio-frequency carrier is overmodulated by an audio frequency signal to produce periodic bursts of radio-frequency energy whose repetition rate corresponds to the frequency of the signal. The output of the unit is fed by a flexible coaxial cable to a tank circuit tuned to the carrier frequency and housed within the barrel of a portable applicator gun on whose grip is mounted a trigger switch operatively connected to the unit. Supported within the barrel and coupled to the tank circuit is a discharge electrode whose tip is adjacent the mouth of the barrel. When an operator holding the gun actuates the trigger switch, the unit is turned out and a corona discharge beam is then projected from the electrode tip, the operator positioning the gun to direct the beam toward the skin surface to be treated.

9 Claims, 2 Drawing Sheets

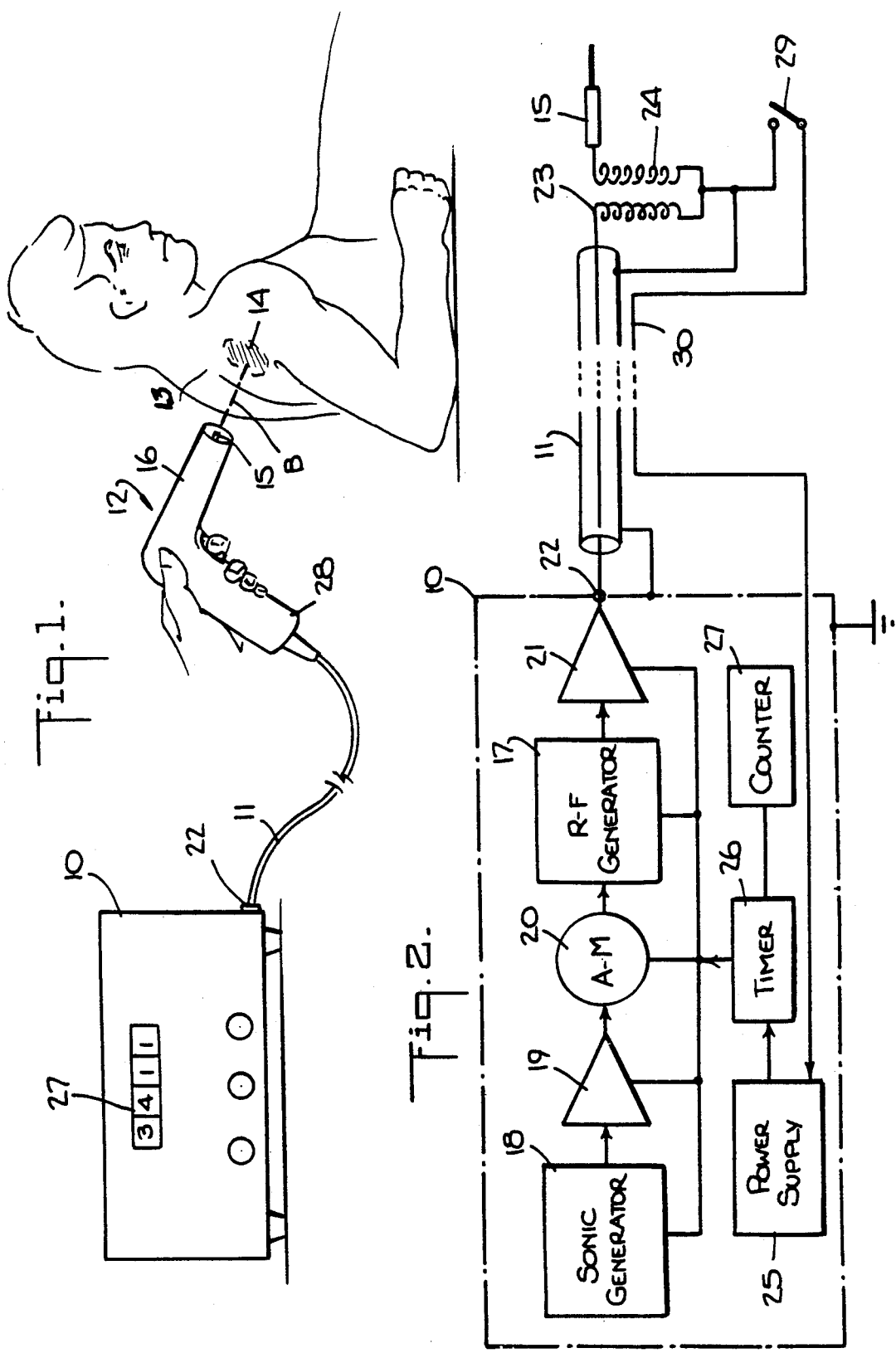

CORONA DISCHARGE BEAM THERMOTHERAPY SYSTEM

BACKGROUND OF INVENTION

1. Field of Invention

This invention relates generally to thermotherapy, and in particular to a corona discharge thermotherapy system for relieving pain and obtaining other salutary effects in which the skin surface of a living body overlying a problem region is subjected to a corona discharge beam derived from periodic bursts of radio-frequency energy whose repetition rate is at a sonic frequency.

2. Status of Prior Art

The term "problem region" as used herein refers to a set of muscles, an arthritic joint or any other region underlying the skin of a patient which is causing difficulty and which lends itself to treatment by thermotherapy.

The interior of the human body has a normal temperature level which is usually said to be 98.6° F. But actually, in the course of each 24-hour period, the body temperature rises above or falls somewhat below this nominal value. Body temperature is determined by the relationship existing between the amount of heat internally generated, which depends on basal metabolism and the amount of heat escaping from the body. Additional heat is produced as a result of muscular activity, this being dissipated by an increase in radiation, conduction or evaporation from the skin surface and by more rapid and deep breathing. If the heat produced by the body surpasses heat losses therefrom, this gives rise to fever.

Medical practitioners since ancient times have known that the application of heat to the body is useful in the relief of muscle soreness and various aches and pains, as well as in the treatment of certain pathological conditions. Thus the use of heat for the treatment of arthritis and other abnormalities is now commonplace. Hot water bottles and electrical heating pads are in widespread use, not merely to provide warmth, but also to afford a degree of relief or therapy for various conditions. In applying heat to the surface of the body, one may do so by convection, by direct contact with a warmed substance; that is, by conduction, or by radiating energy into the body by means of infrared lamps.

As pointed out in chapter 10, "Therapeutic Heat" in the text *Therapeutic Heat and Cold*, edited by Justus F. Lehmann and published in 1982 by Williams and Wilkins, it is generally accepted that heat produces desirable therapeutic effects, for it increases the extensibility of collagen tissues, it decreases joint stiffness, and it affords pain relief. Moreover, heat relieves muscular spasms, it aids in the resolution of inflammatory infiltrates, edema and exudates, and it enhances blood flow.

The exact physiological mechanisms by which applied heat creates soothing and analgesic effects are not known. However, regardless of how heat is generated, the results within the heated tissue are essentially the same, for heat produces a rise in the temperature of the tissue with a concomitant increase in metabolism. As a consequence, there is a relative increase in the accumulation of metabolic wastes such as carbon dioxide and acid metabolites. And because heat acts as a vasodilator, this dilation results in increased local circulation and leads to improved cellular nutrition and to an enhanced exchange of wastes. Further benefits are obtained because a greater number of phagocytes and antibodies are carried by the blood into the region being heated.

A system in accordance with the invention makes use of conversive heating which involves the transformation of some other form of energy into heat. The most commonly used sources of such energy are radio waves in the short wave and the microwave bands of the electromagnetic wave spectrum, and ultrasonic energy. Shortwave diathermy uses radio waves in the 10 to 100 MHz frequency range, the human tissues being treated with high-frequency current, either by way of induction or conduction. In microwave diathermy, the frequency is usually about 2500 MHz. While shortwave diathermy tends to spread widely in the body tissues, microwaves are quasi-optical and can be focused and directed for the heating of small selective areas.

Ultrasonic therapy employs high-frequency sound waves, but this energy is selective in its heating properties. Because ultrasonic energy is reflective at interfaces in the body, in excessive dosages it may be destructive.

A system in accordance with the present invention involves a therapeutic technique in which a corona discharge beam is created by applying to a discharge electrode bursts of radio-frequency energy whose repetition rate is at a sonic frequency. Hence, of background interest are the Di Mino U.S. Pat. Nos. 3,676,633 and 3,617,684, in which a corona discharge beam is applied to a resistor in a printed circuit so as to change the ohmic value thereof. These Di Mino patents, however, have nothing to do with thermotherapy.

Of greatest prior art interest is the Di Mino U.S. Pat. No. 4,667,677, which discloses a unit for generating a corona discharge beam and for projecting this beam toward the skin surface of a living body (human or animal) overlying a problem region, the beam serving to relieve pain and gain other salutary effects. The Di Mino unit includes a radio-frequency carrier generator which is overmodulated with an audio-frequency signal to produce periodic bursts of radio-frequency energy whose repetition rate corresponds to the frequency of the signal. These bursts are stored in a tank circuit coupled to the output of the modulated radio-frequency carrier generator. Connected by a short cable to the output of the tank circuit is a hand-held discharge electrode from which is projected a corona discharge beam, the electrode being manipulated by the operator to scan the skin surface to be treated.

The discharge electrode in the arrangement disclosed in Di Mino U.S. Pat. No. 4,667,677 must be in close proximity to the tank circuit included in the energy-generating unit, for if the cable extending between the discharge electrode and the tank circuit is long, the resultant loss of energy will be such as to militate against the production of the corona discharge beam. As a consequence, the energy-generating unit which includes the tank circuit must be adjacent the patient being treated. This creates difficulties in treating a patient; for if the region to be treated is in the neck or shoulder area, the patient may then have to crouch so as to bring the area of interest next to the discharge electrode. In the Di Mino patent arrangement, because the cable between the unit and the discharge electrode is necessarily short, the operator is not free to orient the electrode with respect to any body site, but must instead position the body site so that it is adjacent to the electrode.

Another drawback of the Di Mino unit is that it runs continuously; hence there is a danger in treating a patient with a corona discharge beam that excessive heat will be induced in the problem region, and this may be injurious to the patient. While the patient will sense when the heat is excessive, he may assume that the pain which accompanies excessive heat is a normal part of the treatment and therefore fail to instruct the operator to withdraw the corona discharge beam from the skin surface. And when the patient is an animal who is being restrained, the operator may not be able to sense the animal's reaction to excessive heat.

SUMMARY OF INVENTION

In view of the foregoing, the main object of this invention is to provide a corona discharge beam thermotherapy system for relieving pain and obtaining other beneficial effects by subjecting the skin surface of a living body overlying a problem region with a corona discharge beam derived from a radio-frequency power source, the system including a portable applicator gun connected by a long, flexible cable to an energy-generator unit and provided with a discharge electrode from which the beam is projected, whereby an operator holding the gun can direct the beam toward the skin surface to be treated regardless of its location on the body.

More particularly, an object of this invention is to provide a system of the above type in which the radio-frequency power source is an energy-generating unit in which a radio-frequency carrier whose frequency falls within a low frequency band (100,000 to 1,000,000 Hz) is overmodulated by an audio-frequency signal to produce periodic bursts of radio-frequency energy.

Also an object of this invention is to provide in a system of the above type a portable applicator gun which includes a discharge electrode from which the corona discharge beam is projected, the gun including a trigger switch that is connected to the energy-generating unit which is turned on only when the trigger switch is actuated by the operator holding the gun.

Yet another object of the invention is to provide an energy-generating unit that includes a timer functioning to cyclically activate the unit for a predetermined time period during which a corona discharge beam is produced, successive cycles being separated by a shorter relaxation interval whereby overheating of the problem region is prevented.

Briefly stated, these objects are attained in a corona discharge beam thermotherapy system adapted to project the beam onto the skin surface of a living body overlying a problem region, the beam serving to relieve pain and to obtain other beneficial effects. The system includes an energy-generating unit in which a radio-frequency carrier is overmodulated by an audio frequency signal to produce periodic bursts of radio-frequency energy whose repetition rate corresponds to the frequency of the signal.

The output of the unit is fed by a flexible coaxial cable to a tank circuit tuned to the carrier frequency and housed within the barrel of a portable applicator gun on whose grip is mounted a trigger switch operatively connected to the unit. Supported within the barrel and coupled to the tank circuit is a discharge electrode whose tip is adjacent the mouth of the barrel. When an operator holding the gun actuates the trigger switch, the unit is turned out and a corona discharge beam is then projected from the electrode tip, the operator positioning the gun to direct the beam toward the skin surface to be treated.

OUTLINE OF DRAWINGS

For a better understanding of the invention as well as other objects and further features thereof, reference is made to the following detailed description to be read in conjunction with the accompanying drawings, wherein:

FIG. 1 illustrates the basic components of a corona discharge beam thermotherapy system in accordance with the invention;

FIG. 2 is a block diagram showing the various stages of the energy-generating unit included in the system and the applicator gun coupled to the output of the unit;

DESCRIPTION OF INVENTION

The Basic System

Figure 4:
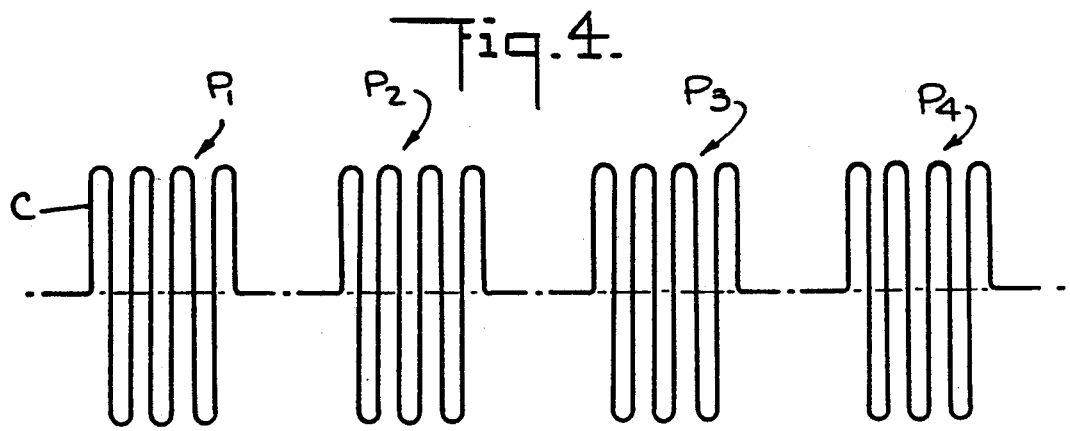
FIG. 4 illustrates the waveform of the bursts of radio-frequency energy produced in the energy generating unit.
Figure 3:
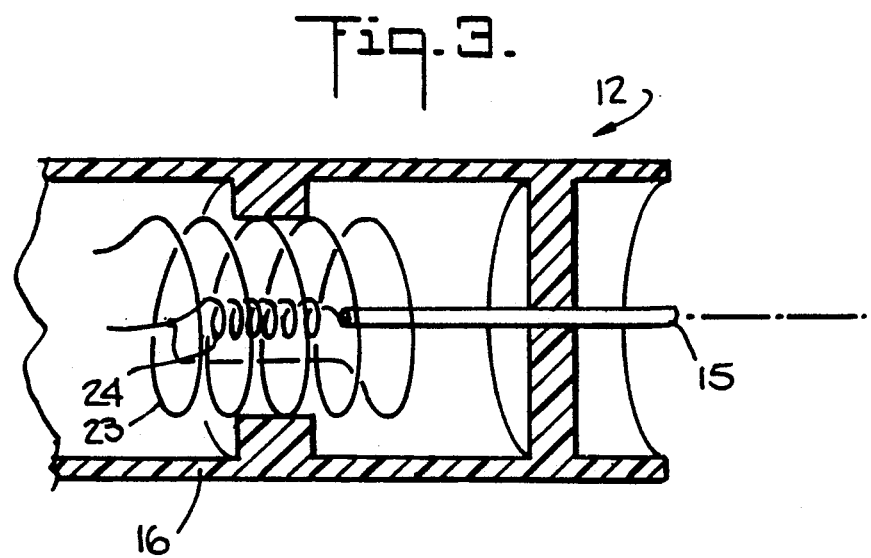
FIG. 3 is a section taken through the barrel of the gun, showing the components housed therein.

Referring now to FIG. 1, a system in accordance with the invention makes use of an energy-generating unit 10 which yields periodic bursts of radio-frequency energy whose repetition rate is at a sonic frequency. This energy is applied via a long, flexible coaxial cable 11 to a hand-held portable applicator gun 12 within whose barrel 16 is mounted a discharge electrode 15 from which is projected a corona discharge beam B. Beam B is directed toward the skin surface 13 of a patient that overlies a problem region 14.

The tip of electrode 15, which is adjacent the mouth of gun barrel 16, is placed within a few centimeters of the skin. The distance between the electrode tip and the skin is such that the clearly visible portion of the corona discharge beam is slightly spaced from the skin, but the less visible portion which projects therefrom engages the skin. The energy is absorbed by the underlying tissue in the problem region 14 of the patient and converted into therapeutic heat. Because of the corona discharge beam, the zone of engagement is small, and in order to irradiate a relatively large skin area, the beam is scanned over this area so that the entire problem region therebelow is subjected to treatment.

A corona discharge is a highly active glow region surrounding a discharge electrode. When the electrode is a pointed wire or rod as in the present case, this glow region extends a short distance beyond this point. Assuming the wire is negatively charged, the free electrons in the air in the region in the intense electric field surrounding the wire gains energy in this field to produce positive ions and other electrons by collision. In turn, these new electrons are accelerated and produce further ionization. This cumulative process results in an electronic avalanche in which the positive ions are accelerated toward and bombard the charged wire. As a consequence of such ionic bombardment, secondary electrons are ejected from the tip of the electrode which act to sustain the corona discharge.

When the voltage applied to the discharge electrode is elevated to a level exceeding the point at which a stable corona discharge is maintained, the air dielectric then completely breaks down to cause a spark discharge. In order to produce a corona discharge, the peak voltage on the discharge electrode must be relatively high but below the level resulting in a spark discharge.

The continuous application of a low radio-frequency energy of relatively low power will not result in a corona discharge. But because in the energy-generating unit 10, the continuous radio-frequency carrier is produced in bursts which shock excite a tank coil included in the unit, the resultant energy surges have a peak amplitude sufficient to produce a sustained corona discharge beam.

The Energy Generating Unit

Referring now to FIG. 2, the energy generating unit 10 includes a radio-frequency generator 17 producing an R-F carrier lying in the low frequency range of 200,000 to 450,000 Hz. In practice, this generator is frequency controlled by a piezoelectric crystal oscillator operating, at, say, 200 KHz, the carrier generator also being stabilized as to amplitude. A conventional low radio-frequency generator may be used for this purpose.

Also included in the unit is an audio-frequency generator 18 operating in the audio-frequency range of 3000 to 5000 Hz to produce a sonic signal. This is amplified in amplifier 19 and applied to an amplitude modulator 20, which is so connected to radio-frequency generator 17 as to effect amplitude modulation of the R-F carrier. Audio-frequency generator 18 is preferably a shielded, solid-state, transistorized oscillator.

In amplitude-modulation, the amplitude of the radio-frequency carrier is varied in accordance with the signal, the resultant modulated wave containing side bands that are the sum and difference of the carrier and signal frequencies. If the modulation index "M" is zero, no signal information is conveyed to the carrier. When, however, $M=1$ (100% modulation), then in the case of a sinusoidal carrier wave, the envelope of the carrier varies from zero to twice the value of its unmodulated amplitude. But if "M" exceeds unity, the carrier is then overmodulated, as a consequence of which the carrier is periodically interrupted at a repetition rate in accordance with the audio-frequency signal.

In the present invention, as shown in FIG. 4, the radio frequency carrier C is overmodulated by the sonic frequency signal, this resulting in periodic bursts $P_1$, $P_2$, $P_3$, etc. of radio-frequency energy whose repetition rate is at the sonic frequency. These bursts of energy from R-F generator 17 are applied through an output amplifier 21 to the output jack 22 of the energy-generator unit.

Plugged into output jack 22 of the energy generating unit 10 is one end of coaxial cable 11 which connects the output of the unit to the tank coil 23 of a tank circuit housed within the barrel 16 of the applicator gun, the tank coil being tuned to the carrier frequency of the unit. Tank coil 23 is inductively coupled to an output coil 24 to which is connected the discharge electrode 15. It is to be noted that the outer shielding conductor of the coaxial cable 11 is grounded, the inner conductor connecting one end of the tank coil 23 to output jack 22, the other end of the tank coil and the corresponding end of the output coil being connected to the grounded conductor. Because of this arrangement, there is no radiation from the coaxial cable.

Because tank coil 23 is shock excited by the bursts $P_1$, $P_2$ etc. of the radio-frequency energy, the resultant damped wave surges in coil 23 have a high peak amplitude, and this causes the desired corona discharge to produce a beam which is both visible and audible. The reason it is visible is that the corona beam in the region adjacent the electrode tip produces a blue glow, and the reason it is audible is that the bursts of energy are at a sonic rate and can therefore be heard. In practice, the power output of the system may be in the order of 5 to 15 watts.

We have found that the resultant heat energy induced in a painful region of the human body is capable of relieving this pain within a relatively short period. We have also found that in some instances, a longer exposure of the problem region to the corona discharge beam, in the case of inflammation due to a rheumatoid arthritis condition, will minimize the swelling, and that a marked reduction in swellng will be experienced about 24 hours after such exposure.

Figure 5:
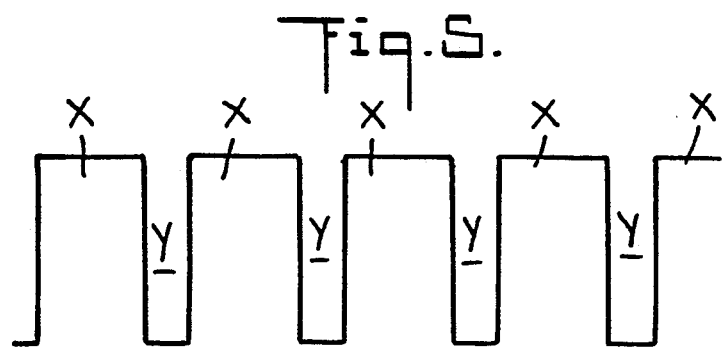
FIG. 5 shows the cylical wave form produced by the timer included in the unit.

Unit 10 is provided with a direct-current power supply 25 whose output is applied to the stages of a unit through a cycle timer switch 26 so that the unit is activated only when the cycle timer switch is "on." The cycle timer switch operation is such as to cyclically activate the unit for a predetermined time period during which a corona discharge beam is produced, successive cycles being separated by a shorter relaxation interval during which the timer switch is off. As shown by the on-off wave in FIG. 5, each cycle X may have a 15-second "on" duration and each relaxation interval a 3-second "off" duration. In practice, other duty cycles may also be efficacious.

The reason for cyclically activating the unit is that during each inactive interval, the heat produced in the body tissue during the preceding active cycle is permitted to be propagated by heat conduction from the skin surface into the interior of the problem region, thereby reducing the skin temperature and avoiding overheating that may occur should the unit be on continuously for a prolonged period. The cyclical operation of the unit also prevents overheating of the unit itself should the unit be kept on continuously for a prolonged period.

The timer also makes it possible to meter the dosage applied to the patient, this being done by means of a digital counter 27 coupled to the timer. Counter 27, which is resettable, counts the number of timing cycles that occur; hence if each cycle has a 15-second duration, followed by a 5-second off interval, then the counter will count three "on" cycles per minute. If, therefore, the operator is instructed for a given treatment to apply a dosage of 10 cycles to a patient, he can readily do so. And the timer-counter arrangement also makes it possible to bill a patient on the basis of the number of cycles of treatment in terms of treatment units (TU).

For billing purposes, the metering arrangement for the unit is preferably of the count-down type, the meter being set at a predetermined fully loaded setting, say, 10,000 TU's. Before treating a patient, the operator first notes the existing meter reading, this depending on the extent to which the unit had previously been put to use. Hence by way of example, we shall assume that the meter reading before treatment of a particular patient is 2,420. Then after the conclusion of this patient's treatment in the course of which the counter counts down, the operator again reads the meter in order to determine the TU's given to the patient. If, therefore, the reading at the start of treatment is 2,420 and at completion the reading is 2,390, then the treatment given this patient is determined by subtracting 2,390 from 2,420 to obtain 30, the number of TU's given to the patient.

Gun 12 is provided with a grip 28 having a trigger switch 29 mounted thereon. This switch, one contact of which is grounded, is connected by a line 30 to power supply 25. In this way, the unit 10 is only turned on when an operator holding the gun 12 in his hand actuates the trigger switch. In practice, the trigger switch may be arranged to actuate a relay having a time delay characteristic, so that once the trigger is momentarily pulled, the unit is turned on for, say, a 15-second interval, and does not release until this interval is completed.

The applicator gun may be shaped like a typical hair blow dryer, and it is even lighter than such a dryer, for all it contains is the tank circuit and the discharge electrode. Because the operator is free to manipulate the gun which is connected to unit 10 by a long cable (say 6 feet in length), he is able to treat any region of a human or animal patient. In treating an animal such as a horse, the audio sound produced by the unit when a corona discharge takes place may startle the animal and make it difficult to treat the animal.

To avoid startling the animal, the unit may include a sound generator which produces a tone at the same frequency as that produced by the corona discharge beam, but somewhat louder. This sound generator can be switched on by the operator before subjecting the animal to treatment so that the animal becomes accustomed to this sound, and when the corona discharge beam is then turned on, its sound has no effect on the animal.

While there has been shown and described a preferred embodiment of a corona discharge beam thermotherapy system in accordance with the invention, it will be appreciated that many changes and modifications may be made therein without, however, departing from the essential spirit thereof.

We claim:

1. A corona discharge beam thermotherapy system adapted to project the beam onto the skin surface of a living body overlying a problem region in a body site, the beam serving to relieve pain, said system comprising:
   (a) an energy-generating unit in which a radio-frequency carrier having a predetermined radio frequency is modulated by an audio-frequency signal having a predetermined audio frequency to produce at an output terminal periodic bursts of radio-frequency energy whose repetition rate corresponds to the frequency of the signal; and
   (b) a portable applicator gun having a barrel provided with an open mouth in which are housed both a tank circuit connected by a relatively long shielded cable extending from the gun to the output terminal of the unit and a discharge electrode, one end of which is coupled to the tank circuit, the other end of the electrode terminating in a tip adjacent the mouth of the barrel and spaced from said skin surface, from which tip is projected said beam which impinges on the skin surface, whereby an operator holding the gun is free to bring the gun into operative relation with any body site on the living body.

2. A system as set forth in claim 1, wherein said unit is provided with a radio-frequency generator to produce said carrier, and audio-frequency oscillator to produce said signal, and means to modulate the carrier with said signal to produce the bursts of energy.

3. A system as set forth in claim 1, wherein said tank circuit includes a tank coil tuned to the frequency of the carrier and connected by said cable to said terminal, and an output coil inductively coupled to the tank coil and connected to the electrode.

4. A system as set forth in claim 1, in which said gun is provided with a grip having a trigger switch mounted thereon and connected by a line which runs along said cable to a power supply for said unit, whereby said unit is activated only when the trigger switch is actuated.

5. A system as set forth in claim 1, wherein said cable is a coaxial cable whose outer conductor is grounded.

6. A system as set forth in claim 1, wherein said unit includes means for producing a carrier lying within a low radio-frequency range whose upper limit is about one million Hz.

7. A system as set forth in claim 1, wherein said unit includes a cycle timer switch means which in the course of operation cyclically activates said unit to produce operating cycles having a predetermined duration, and an inactive interval between successive cycles of shorter duration.

8. A system as set forth in claim 7, wherein said switch means produces operating cycles and intervals, each cycle having a duration of about 15 seconds and each interval a duration of no greater than about 5 seconds.

9. A system as set forth in claim 7, further including a counter coupled to the switch means to count the cycles produced by the switch means in the course of operation.

* * * * *